United States Patent
Kendall et al.

(10) Patent No.: US 7,281,848 B2
(45) Date of Patent: Oct. 16, 2007

(54) X-RAY TUBE MOUNTING METHODOLOGY

(75) Inventors: Charles B. Kendall, Brookfield, WI (US); Carey Shawn Rogers, Brookfield, WI (US)

(73) Assignee: General Electric Co., Schenectady, NY (US)

( * ) Notice: Subject to any disclaimer, the term of this patent is extended or adjusted under 35 U.S.C. 154(b) by 64 days.

(21) Appl. No.: 11/161,793

(22) Filed: Aug. 17, 2005

(65) Prior Publication Data

US 2007/0041507 A1   Feb. 22, 2007

(51) Int. Cl.
*H05G 1/04* (2006.01)
(52) U.S. Cl. ...................................... 378/193
(58) Field of Classification Search ............. 378/193, 378/195–198
See application file for complete search history.

(56) References Cited

U.S. PATENT DOCUMENTS

| | | | |
|---|---|---|---|
| 3,863,994 A * | 2/1975 | Fink | 175/364 |
| 5,032,047 A | 7/1991 | Theakston | 411/104 |
| 5,037,258 A | 8/1991 | Heurteux | 411/104 |
| 6,173,919 B1 | 1/2001 | Le Blaye | 244/54 |
| 6,209,822 B1 | 4/2001 | Le Blaye | 244/54 |
| 6,341,746 B1 | 1/2002 | Pascal | 244/54 |
| 6,457,923 B1 | 10/2002 | Grossman | 411/104 |
| 2005/0175150 A1* | 8/2005 | Smith et al. | 378/119 |
| 2005/0243969 A1* | 11/2005 | Andrews | 378/119 |

* cited by examiner

*Primary Examiner*—Allen C. Ho

(57) ABSTRACT

An imaging assembly is provided comprising an x-ray tube housing having a tube mounting hub and formed from a lightweight material. A rotating gantry assembly includes a gantry mounting surface adapted to engage said tube mounting hub. A plurality of barrel nut fasteners secure the tube mounting hub to the gantry mounting surface while reducing stress in said x-ray tube housing.

12 Claims, 2 Drawing Sheets

X-RAY TUBE MOUNTING METHODOLOGY

TECHNICAL FIELD

The present invention relates generally to an x-ray tube mounting assembly and more particularly to an improved method of mounting an x-ray tube housing to a rotating gantry assembly.

BACKGROUND OF THE INVENTION

Modern medical imaging assemblies have increased in complexity and capabilities. As the complexity and capabilities increase, often so both initial cost and cost of maintenance. This places a premium on assemblies that are simple to assemble and simple to dissemble for maintenance. In the case of imaging assemblies that also incorporate movement and rotation as a part of operation, such as computed tomography (CT) systems, simple assembly and disassembly must also be combined with reliable high strength designs.

CT systems function through the rotation of an x-ray tube assembly around a patient. The centripetal acceleration experienced as a result of such operational rotations generates loading within the rotating components. These reacting loads on the rotating components can rise to significant levels. The reacting loads may be especially of concern in regions containing mounted components wherein the loading may result in undesirable stress generated within the mounting elements or within the structure. Such is the case wherein the x-ray housing assembly is mounted to the rotating gantry. The loading in a CT system is also cyclical and oscillating in amplitude, so mounting designs must be resistant to mechanical fatigue.

Commonly the x-ray housing is mounted to the rotating gantry through the use of blind threaded holes and the use of fastener bolts engaging these tapped holes. The mounted components, however, are often made from lightweight materials such as aluminum and thereby generate strength concerns within the threaded holes. One solution has been to use threaded inserts to increase the strength of the threads above what the aluminum material is capable of generating. The mountings, however, are commonly located in regions wherein space limitations may dictate the size of the fastener and thereby further limit the strength of the assembly.

It would, therefore, be highly desirable to have an x-ray tube mounting assembly that was compatible with the low weight and reduced strength materials commonly found in x-ray tube mounting assemblies. It would further be highly desirable to have an x-ray tube mounting assembly that improved fastener strength even in regions having restrictive space limitations.

SUMMARY OF THE INVENTION

An imaging assembly is provided comprising an x-ray tube housing having a tube mounting hub and formed from a lightweight material. A rotating gantry assembly includes a gantry mounting surface adapted to engage said tube mounting hub. A plurality of barrel nut fasteners secure the tube mounting hub to the gantry mounting surface while reducing stress in said x-ray tube housing.

Other features of the present invention will become apparent when viewed in light of the detailed description of the preferred embodiment when taken in conjunction with the attached drawings and appended claims.

DESCRIPTION OF THE PREFERRED EMBODIMENT(S)

Figure 1:
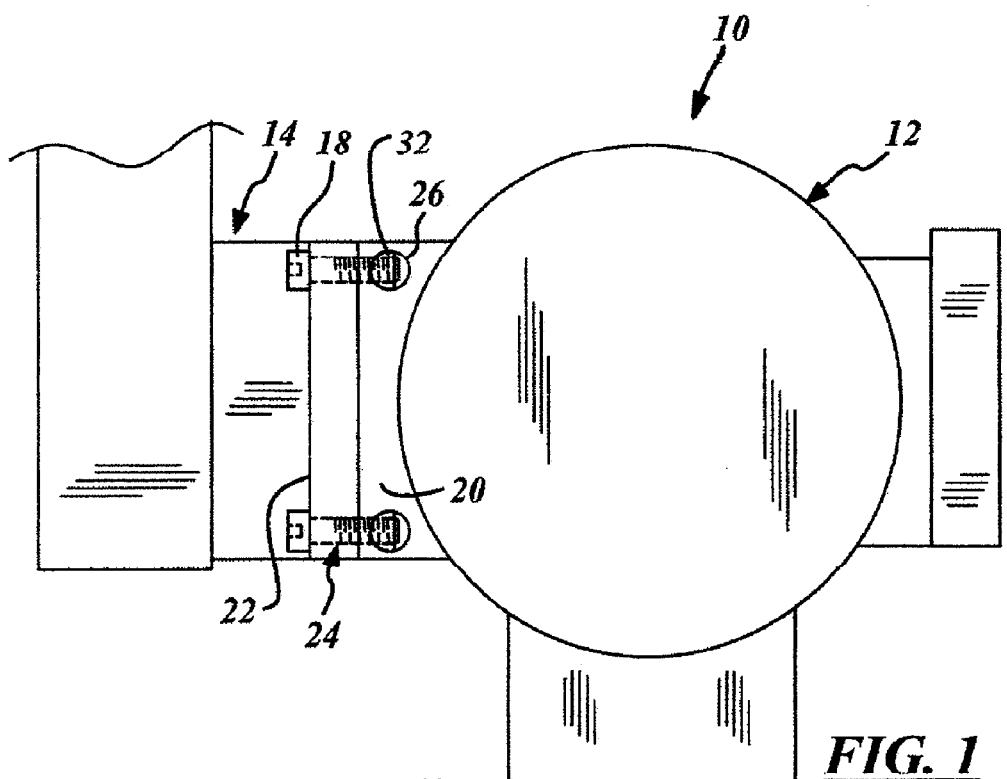
FIG. 1 is an illustration of an imaging assembly in accordance with the present invention.
Figure 2:
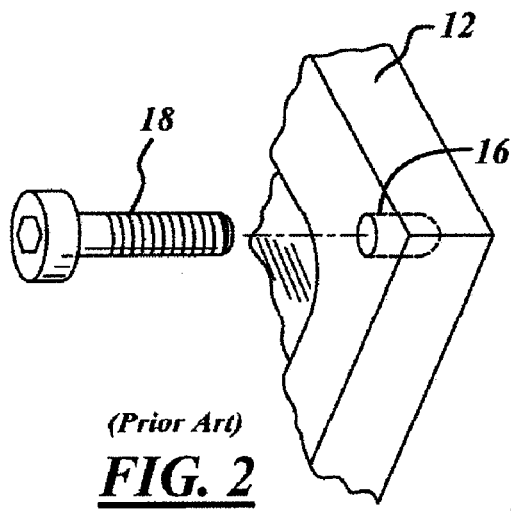
FIG. 2 is an illustration of a prior art mounting methodology.
Figure 3:
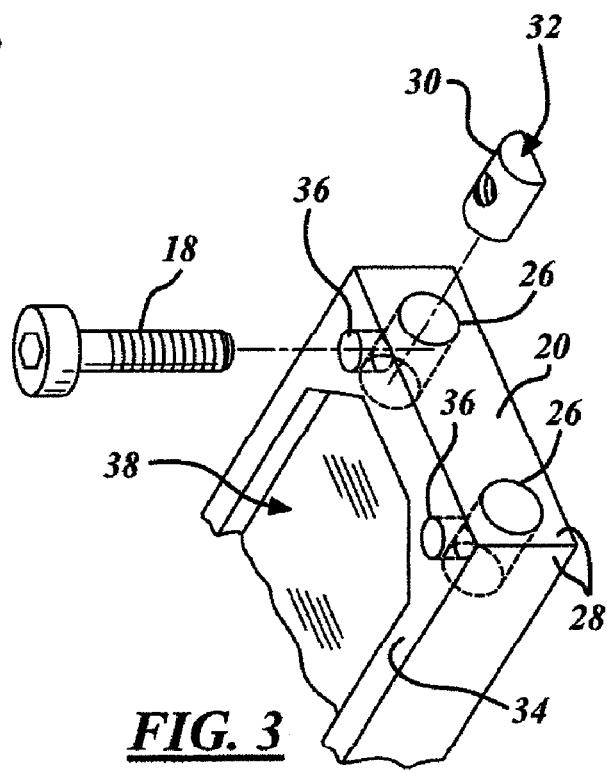
FIG. 3 is an illustration of a barrel nut fastener assembly for use in the imaging assembly shown in FIG. 1.
Figure 4:
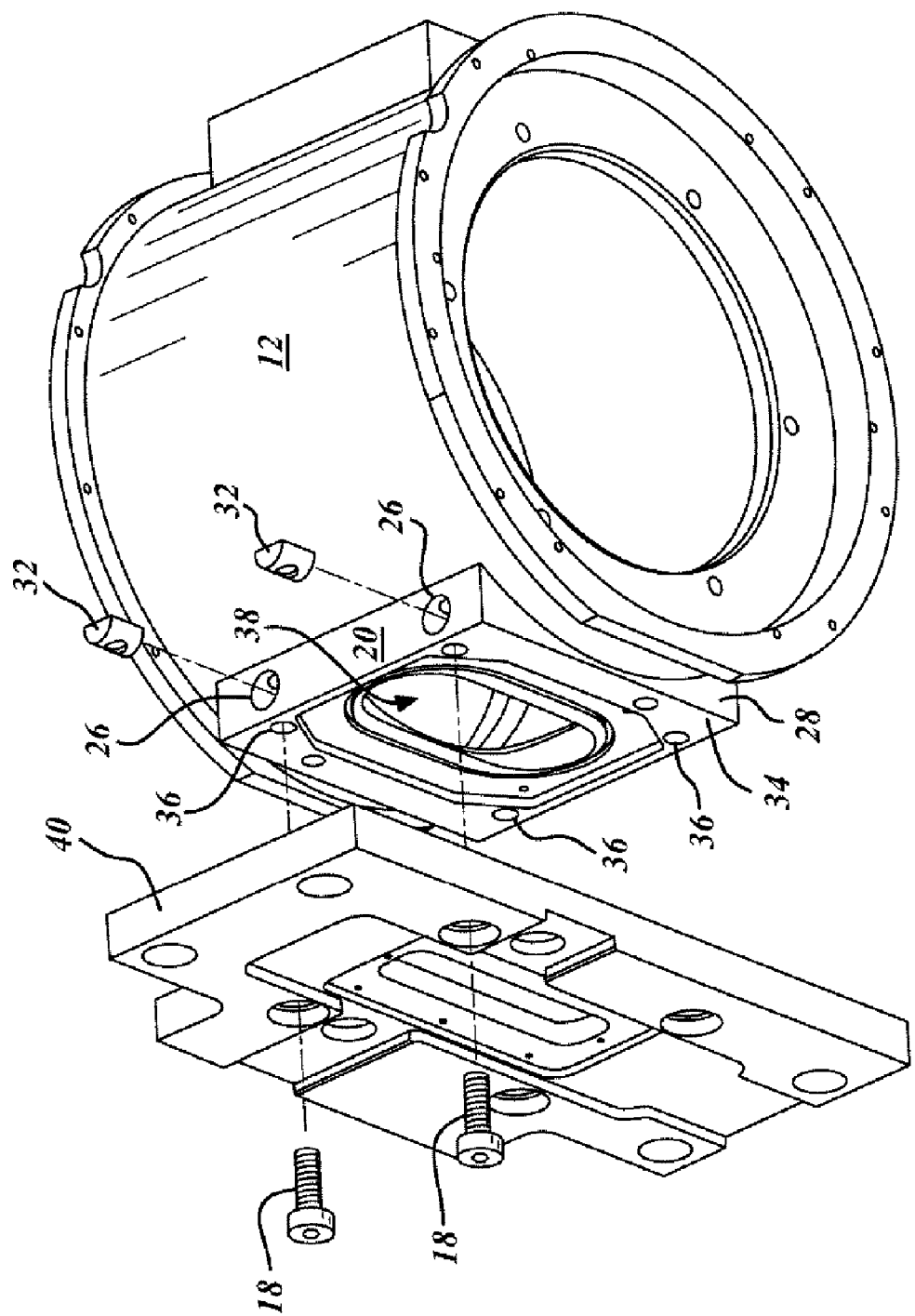
FIG. 4 is a detailed illustration of the imaging assembly shown in FIG. 1, the imaging assembly illustrated including a steel mounting plate.

Referring now to FIG. 1, which is an illustration of an imaging assembly or specifically a computed tomography (CT) x-ray tube assembly 10 for use with the present invention. The assembly 10 includes an x-ray tube housing 12 mounted to a rotating gantry assembly 14. A wide variety of x-ray tube housing 12 and rotating gantry assembly 14 configurations are contemplated by the present invention. The present invention is directed towards an improved methodology of joining the x-ray tube housing 12 to the rotating gantry assembly 14 such that a lightweight material such as aluminum may be utilized to form the housing 12 without a loss of strength or an increase in material fatigue. Existing attachments often use a tapped hole 16 containing threads that is tapped directly into the housing 12. (See FIG. 2). A bolt element 18 is used to engage the tapped hole 16. This is not amenable to usage with lightweight materials wherein the threads of the tapped hole 16 may be damaged or the tapped hole/bolt combination cannot withstand imposed mechanical forces or fatigue life requirements.

The present invention addresses this concern by utilizing a tube mounting hub 20 formed as a portion of the housing 12 (see FIG. 1). The tube mounting hub 20 may be formed from a low strength material The tube mounting hub 20 is designed to directly or indirectly engage a gantry mounting surface 22 on the rotating gantry assembly 14. A plurality of barrel nut fasteners 24 are utilized to secure the tube mounting hub 20 to the rotating gantry assembly 14. The use of barrel nut fasteners 24 allows for a reduction in stresses in the tube mounting hub 20 which in turn allows for the use of lightweight lower strength materials. In addition, the barrel nut fasteners 24 provide a secure attachment even where a degree of misalignment between the tube mounting hub 20 and the gantry assembly 14 exists.

Although the barrel nut fasteners 24 may be attached in a variety of fashions, one embodiment contemplates the formation of barrel nut chambers 26 formed in the plurality of hub side surfaces 28. Each of the barrel nut fasteners 24 comprise a barrel nut element 32 having a semi-cylindrical shape and a curved barrel nut outer surface 30. The curved barrel nut chambers 26 when engaging the curved barrel nut outer surface 30 of the barrel nut elements 32 allow for the degree of misaligmnent previously discussed. The bolt elements 18 enter the hub mounting surface 34 though upper bolt chambers 36 formed therein and intersecting the barrel nut chambers 26. This arrangement spreads the load incurred by the barrel nut elements 32 over a much greater area than simply a tapped hole. It also allows for a much smaller bolt element 18 to be utilized. This is highly valuable where space is so limited as in x-ray tube housing 12 mounts. The barrel nut element 32 is made from a high strength material, thereby improving the bolted joint performance compared to the prior art of direct tapping into lower strength, lightweight material.

The space is often so constricted due to the necessity of having a tube x-ray exit portal 38 formed in the tube mounting hub 20 to allow for unrestricted x-ray fluence from the x-ray tube. The presence of the x-ray exit portal 38, however, often leaves little room between the portal 38 and the hub side surfaces 28. Standard tapping methodologies would leave insufficient material left to support the strain and loading after assembly. The present information allows the upper bolt chamber 36 to be positioned between the portal 38 and the side surfaces 28 with minimal gap while not increasing the strain on the hub material. In addition, the present invention allows for dismantling and reassembly without damage since present tapped methods destroy threads after continuous assembly/disassembly but the present barrel nut fasteners 24 leave the structures unmarked and may even themselves be replaced at inconsequential cost.

Finally, although the hub mounting surface 34 may be mounted directly to the gantry mounting surface 22, it is contemplated that a steel mounting plate 40 may be positioned between the two surfaces. In this embodiment it is contemplated that the tube mounting hub 20 be mounted to the steel mounting plate 40 as described and the steel mounting plate be bolted independently to the rotating gantry 14. In this fashion, the steel mounting plate 40 may be considered a removable portion of the rotating gantry assembly 14. The use of the steel mounting plate 40 allows careful and remote attachment of the x-ray tube housing 12 prior to affixation to the rotating gantry assembly 14.

While particular embodiments of the invention have been shown and described, numerous variations and alternative embodiments will occur to those skilled in the art. Accordingly, it is intended that the invention be limited only in terms of the appended claims.

What is claimed is:

1. An imaging assembly comprising:
    an x-ray tube housing;
    a rotating gantry assembly including a gantry mounting surface, said gantry mounting surface adapted to engage said x-ray tube housing; and
    a plurality of barrel nut fasters securing said x-ray tube housing to said gantry mounting surface, said plurality of barrel nut fasteners reducing stress in said x-ray tube housing;
    wherein each of said plurality of barrel nut fasteners including a barrel nut element having a semi-cylindrical shape; and
    wherein said x-ray tube housing comprises a low-strength, lightweight tube mounting hub adapted to engage said gantry mounting surface; and a plurality of barrel nut chambers formed in said low-strength, lightweight tube mounting hub, each of said plurality of barrel nut fasteners including a bolt element and said barrel nut element, said plurality of barrel nut elements positioned within said plurality of barrel nut chambers;
    said imaging assembly further comprising:
    a steel mounting plate mounted between said low-strength, lightweight tube mounting hub and said gantry mounting surface, said plurality of barrel nut fasteners securing said low-strength, lightweight tube mounting hub to said steel mounting plate, said steel mounting plate secured to said gantry mounting surface.

2. An imaging assembly as described in claim 1, wherein each of said barrel nut elements having a curved barrel nut outer surface and mounted within a barrel nut chamber such that said x-ray tube housing is secured to said rotating gantry assembly even if said x-ray tube housing is slightly misaligned.

3. An imaging assembly as described in claim 1, wherein said x-ray tube housing is comprised of an aluminum alloy.

4. An imaging assembly as described in claim 1, wherein said x-ray tube housing comprises a low-strength tube mounting hub adapted to engage said gantry mounting surface, said low-strength tube mounting hub having a hub mounting surface and a plurality of hub side surfaces, at least one upper bolt chamber formed in said hub mounting surface, and at least one barrel nut chamber formed in at least one of said plurality of hub side surfaces, said at least one upper bolt chamber positioned in close proximity to at least one of said plurality of hub side surfaces, and wherein said at least one barrel nut chamber intersecting said at least one upper bolt chamber.

5. An imaging assembly as described in claim 4, further comprising:
    a tube x-ray exit-portal formed in said low-strength tube mounting hub, said at least one upper bolt chamber positioned between said tube x-ray exit portal and at least one of said plurality of hub side surfaces.

6. An imaging assembly comprising:
    an x-ray tube housing including a tube mounting hub, said x-ray tube housing formed from a lightweight material;
    a rotating gantry assembly including a gantry mounting surface, said gantry mounting surface adapted to engage said tube mounting hub; and
    a plurality of barrel nut fasteners securing said tube mounting hub to said gantry mounting surface, said barrel nut fasteners reducing stress in said x-ray tube housing;
    wherein each of said plurality of barrel nut fasteners including a barrel nut element having a semi-cylindrical shape;
    wherein said tube mounting hub comprises a plurality of upper bolt chambers formed in a hub mounting surface and a plurality of barrel nut chambers formed in at least one hub side surface, each of said plurality of barrel nut chambers intersecting one of said plurality of upper bolt chambers; and
    wherein each of said plurality of barrel nut fasteners comprising a bolt element positioned in one of said plurality of upper bolt chambers and a barrel nut element positioned in one of said plurality of barrel nut chambers, each of said plurality of barrel nut elements engaging one of said plurality of bolt elements to removably secure said tube mounting hub to said gantry mounting surface;
    said imaging assembly further comprising:
    a steel mounting plate mounted between said tube mounting hub and said gantry mounting surface, said plurality of barrel nut fasteners securing said tube mounting hub to said steel mounting plate, said steel mounting plate secured to said gantry mounting surface.

7. An imaging assembly as described in claim 6, wherein each of said plurality of barrel nut elements comprising a curved barrel nut outer surface, and wherein each of said plurality of barrel nut chambers comprising a curved barrel nut chamber such that each of said plurality of barrel nut elements can rotate within each of said plurality of barrel nut chambers, and such that said x-ray tube housing is secured to said rotating gantry assembly even when misaligned.

8. An imaging assembly as described in claim 6, wherein said x-ray tube housing is comprised of an aluminum alloy.

9. An imaging assembly as described in claim 6, wherein each of said plurality of upper bolt chambers is positioned in close proximity to said at least one hub side surface.

10. An imaging assembly as described in claim 6, further comprising:
   a tube x-ray exit portal formed in said tube mounting hub, each of said plurality of upper bolt chambers positioned between said tube x-ray exit portal and said at least one hub side surface.

11. A method of constructing an imaging assembly comprising:
   forming an x-ray tube housing including a tube mounting hub from a lightweight material;
   removably mounting said tube mounting hub to a rotating gantry assembly by:
   placing a steel mounting plate between said tube mounting hub and a gantry mounting surface of said rotating gantry assembly;
   inserting a bolt element through said steel mounting plate and into an upper bolt chamber formed in a hub mounting surface of said tube mounting hub;
   inserting a barrel nut element into a barrel nut chamber formed into a hub side surface such that said barrel nut chamber intersects said upper bolt chamber;
   engaging said bolt element with said barrel nut element such that said tube mounting hub is secured to said steel mounting plate; and
   securing said steel mounting plate to said gantry mounting surface such that said x-ray tube housing is secured to said rotating gantry assembly.

12. A method as described in claim 11, further comprising:
   forming a tube x-ray exit portal in said tube mounting hub, said upper bolt chamber positioned between said tube x-ray exit portal and said hub side surface.

* * * * *